United States Patent [19]

Samuels et al.

[11] Patent Number: 5,203,328

[45] Date of Patent: Apr. 20, 1993

[54] APPARATUS AND METHODS FOR QUANTITATIVELY MEASURING MOLECULAR CHANGES IN THE OCULAR LENS

[75] Inventors: Mark A. Samuels, Duluth; Scott W. Patterson, Lawrenceville; Jonathan A. Eppstein, Atlanta, all of Ga.; Nai T. Yu, Kowlon, Hong Kong; Sven-Erik Bursell, Newton, Mass.

[73] Assignee: Georgia Tech Research Corporation, Atlanta, Ga.

[21] Appl. No.: 731,533

[22] Filed: Jul. 17, 1991

[51] Int. Cl.$^5$ ............................ A61B 5/00; A61B 3/10
[52] U.S. Cl. ...................................... 128/633; 351/221
[58] Field of Search ................. 128/633, 665; 351/221; 356/318

[56] References Cited

U.S. PATENT DOCUMENTS

| | | | |
|---|---|---|---|
| 4,548,498 | 10/1985 | Folestad et al. | 356/318 |
| 4,582,405 | 4/1986 | Müller et al. | |
| 4,592,361 | 6/1986 | Parker et al. | 128/633 |
| 4,675,300 | 6/1987 | Zare et al. | 436/172 |
| 4,702,576 | 10/1987 | Magnante | |
| 4,711,540 | 12/1987 | Yoshino et al. | |
| 4,711,541 | 12/1987 | Yoshino et al. | |
| 4,711,542 | 12/1987 | Ichihashi et al. | |
| 4,758,081 | 7/1988 | Barnes | 606/4 |
| 4,776,687 | 10/1988 | Nakanishi et al. | |
| 4,781,453 | 11/1988 | Kobayashi | |
| 4,836,207 | 6/1989 | Bursell et al. | |
| 4,838,683 | 6/1989 | Ichihashi et al. | |
| 4,848,897 | 7/1989 | Aizu et al. | |
| 4,852,987 | 8/1989 | Lohmann | |
| 4,854,693 | 8/1989 | Ichihashi et al. | |
| 4,883,351 | 11/1989 | Weiss | 351/221 |
| 4,895,159 | 1/1990 | Weiss | 128/665 |
| 4,950,068 | 8/1990 | Mizuta | |

FOREIGN PATENT DOCUMENTS

261957A1 11/1988 Fed. Rep. of Germany.

OTHER PUBLICATIONS

G. Bessems, et al., "Non-Tryptophan Fluorescence of Crystallins From Normal and Cataractous Human Lenses," *Investigative ophthalmology & Visual Science*, Jul. 1987, vol. 28, pp. 1157-1163.

J. Bleeker, et al., "Autofluorescence of the Lens in Diabetic and Healthy Subjects by Fluorophotometry," *Investigative Ophthalmology & Visual Science*, May 1986, vol. 27, No. 5, pp. 791-794.

J. Helve, et al., "Autofluorescence of the Human Diabetic Lens in Vivo," *American Journal of Ophthalmology*, Apr. 1976, vol. 81, No. 4, pp. 491-494.

(List continued on next page.)

*Primary Examiner*—Lee S. Cohen
*Assistant Examiner*—Kevin Pontius
*Attorney, Agent, or Firm*—Kilpatrick & Cody

[57] ABSTRACT

Apparatus and methods for noninvasively diagnosing diabetes mellitus, the prediabetic condition, and cataracts in the human (or other) body are disclosed. Diagnoses are made by illuminating ocular lens tissue with a narrow-band light source at a selected wavelength, detecting the backscattered radiation intensity at the peak of the fluorescent response, and normalizing the detected value with the intensity of its Rayleigh component. Measurements provided in this manner can be used as improved indicators of the presence or absence of certain diseases or conditions.

16 Claims, 4 Drawing Sheets

OTHER PUBLICATIONS

Hockwin, et al., "Investigations on Lens Transparency and its Disturbances by Microdensitometric analysis of Scheimpflug Photographs," *Current Eye Research*, 1984, vol. 3, No. 1, pp. 15-22.

R. Jacobs, et al., "Fluorescence Intensity Profile of Human Lens Sections," *Investigative Ophthalmology & Visual Science*, Jan. 1981, vol. 20, No. 1, pp. 117-120.

R. Lendrum, et al., "Islet-Cell Antibodies in Diabetes Mellitus," *The Lancet*, Dec. 11, 1976, pp.1273-1275.

S. Lerman, et al., "Ultraviolet-Visible Slit Lamp Densitography of the Human Eye," *Exp. Eye Research*, 1981, vol. 33, pp. 587-596.

W. Lohmann, et al., "Device for Measuring Native Fluorescence of Lenses," *Journal of Biochemical and Biophysical Methods*, 1988, vol. 17, pp. 155-158.

W. Lohmann, et al., "Distribution Pattern of Native Fluorophores in Cataractous Lenses," *Exp. Eye Research*, 1990, vol. 50, pp. 227-230.

M. Mosier, et al., "Autofluorescence of the Crystalline Lens in Diabetes," *Arch. Ophthalmology*, Sep. 1986, vol. 104, pp. 1340-1343.

J. van Best, et al., "In vivo Assessment of Lens Transmission for Blue-Green Light by Autofluorescence Measurement," Ophthalmic Research, 1985, vol. 17, pp. 90-95.

J. van Best, et al., "Autofluorescence and Light Scatter in the Human Lens as Measured by a Fluorophotometer," *Exp. Eye Research*, 1989, vol. 49, pp. 511-513.

N. Yu, "Clinical Monitor of Diabetic Lenses by Fluorescence/Raman," Grant No. EY07006-01, May 1986.

N. Yu, "Clinical Monitor of Diabetic Lenses by Fluorescence," Continuation grant no. EY07006-02, Jan. 1988.

N. Yu, "Clinical Monitor of Diabetic Lenses by Fluorescence," Progress report summary-grant No. EY07006-04, Jan. 1990.

N. Yu, et al., "Progress Report," Apr. 1991.

APPARATUS AND METHODS FOR QUANTITATIVELY MEASURING MOLECULAR CHANGES IN THE OCULAR LENS

This invention relates to evaluating changes in biological tissues and more specifically to apparatus and methods for quantitatively measuring molecular changes in the lens of the eye.

BACKGROUND OF THE INVENTION

Existing methods for diagnosing diseases, particularly diabetes, are often less than desirable. One such method, the oral glucose tolerance test, attempts to assist diagnosis of diabetes mellitus by determining whether elevated blood glucose levels exist in patients suspected of having the disease. Because many patients having elevated levels fail subsequently to develop the clinical symptoms of the disease, however, the reliability of the test is generally questioned.

A second diagnostic method, the Islet Cell Antibody (ICA) test, may be used to predict those patients at risk for type I diabetes and can predate the onset of debilitating clinical symptoms by as much as five years. The ICA test is not typically utilized, however, because of its complexity, expense, and lack of specificity and because of a lack of standardization among evaluating laboratories. Furthermore, the test is useful only for detecting type I diabetes, which strikes only approximately ten percent of the entire diabetic patient population. By contrast, patients suspected of having the prediabetic condition for type II diabetes currently have no confirming diagnostic procedure.

It is well known that certain portions of the eye fluoresce when illuminated. The lens of the eye, for example, can be made to fluoresce intensely when illuminated with radiation having a wavelength between approximately 350 nm and 550 nm. Utilizing radiation of a wavelength less than approximately 400 nm typically is avoided (unless power levels and exposure times are restricted), however, since this higher frequency radiation is known to cause damage to ocular tissue.

The presence of certain diseases in the human body cause chemical changes in the lens of the eye, altering the amount of the fluorescent response to an illumination of the lens. The lenses of cataract patients, for example, become opaque due to lipid peroxidation, protein glycosylation, and the conversion of sulfhydryl (—SH) bonds to disulfide bonds (—SS). Similarly, in diabetes mellitus and galactosemia, the glucose and galactose are converted to sorbitol and dulcitol, respectively. Accumulation of these compounds results in a high osmotic gradient within the lenticular cells. Prolonged therapy with drugs such as corticosteroids and chlorpromazine also causes opacities of the human lens.

U.S. Pat. Nos. 4,895,159 and 4,883,351 to Weiss (which patents are incorporated herein in their entireties by this reference), thus, disclose methods for detecting the existence of diabetes using light scattered from lenticular cells. As described in the Weiss patents, the backscattered light from a patient suspected of having diabetes is used to calculate a diffusion coefficient for that patient. A second determination of diffusion coefficients is made for a control group of nondiabetic patients, and the diffusion coefficient of the suspected diabetic is compared with those of nondiabetic, control group patients of the same age.

Because lenses typically cloud naturally as patients age, however, measurements made in connection with the methods of the Weiss patents can be taken only from clear sites in the patients' lenses. The Weiss techniques also appear unable to distinguish the ultimate cause of changes in diffusion coefficients or to detect the prediabetic condition (i.e. where no overt clinical signs of diabetes are displayed but will be exhibited within approximately five years as, for example, when a positive ICA test occurs), since myriad diseases and physiological conditions are known to affect the lens in the manner therein described. Use of the diffusion coefficient as a stand-alone diagnostic test also suffers from its variability as a function of patient age, particularly since results have both age-dependent and age-independent variance.

Other patents, such as West German Patent No. 261957A1 to Schiller and U.S. Pat. No. 4,852,987 to Lohmann (each of which is incorporated herein in its entirety by this reference), describe alternate diagnostic methods in which the fluorescence signal intensities are compared. The Schiller patent, for example, discloses comparing fluorescence signal intensities at two wavelengths using a single excitation wavelength in an effort to detect the presence of cataracts. The ratio of the resulting fluorescence intensities is compared to the ratio obtained at the same wavelengths from known cataract patients to achieve the desired diagnostic result. As described in the Schiller patent, the excitation wavelengths are selected from the ranges 320-340 nm, 380-390 nm, and 430-450 nm, while the intensity of fluorescence peaks is measured within wavelength ranges of 410-440 nm, 450-460 nm, and 500-520 nm. In contrast to the Schiller patent, the Lohmann patent measures the magnitude of fluorescence intensity at a single wavelength created by light of one excitation wavelength and compares this intensity to known intensities at the given wavelengths in order to determine the degree of eye lens cloudiness. Neither of these patents, however, teaches or suggests detection of diabetes or the prediabetic condition.

SUMMARY OF THE INVENTION

The present invention provides apparatus and methods for noninvasively diagnosing selected diseases, including diabetes and the prediabetic condition, in tissues of humans or other animals. Utilizing a narrow-band light source of wavelength between 400-430 nm (and, preferably, approximately 406.7 nm) from a laser or similar device and a confocal lens system, the present invention illuminates the ocular lens tissue and determines the intensity of the backscattered radiation at both the peak of the fluorescent response (typically at approximately 490 nm within the range 460-500 nm) and the peak of the Rayleigh component (at the excitation wavelength). The detected radiation subsequently is transmitted to a spectrometer to be divided into its various components (e.g. fluorescence and Rayleigh). The intensity of the fluorescent component is then normalized to the intensity of the Rayleigh component by forming the ratio of the fluorescent intensity to the Rayleigh intensity. The relative amounts of the backscattered fluorescent and Rayleigh radiation provide a reliable indicator of the onset and progression of diseases such as diabetes mellitus, the prediabetic condition, and cataracts in the human or other body.

Unlike existing techniques such as those described above, the present invention essentially eliminates the age-dependent measurement variations previously shown to be present. By measuring the Rayleigh component of the backscattered radiation and using it for normalization, the precise amount of illumination energy delivered to the subject lens tissue area relative to the amount of fluorescence signal generated by the tissue can be determined. This approach reduces complications associated with variances in lens opacity which can alter, in an unknown fashion, the level of illumination delivered to the subject area. By diminishing the effect of the subjects' ages on the test results, the technique permits establishment of a clear threshold—independent of age—separating the diabetic and prediabetic patients from those without the disease. The invention also neither requires use of a coherent light source nor suffers from the lack of specificity (existing in, e.g., the Weiss techniques) in discriminating the ultimate cause of the effect being measured.

It is therefore an object of the present invention to provide apparatus and methods for noninvasively diagnosing diabetes mellitus, the prediabetic condition, cataracts, and the presence of other diseases.

It is another object of the present invention to provide apparatus and methods permitting normalization of a fluorescence signal scattered from a subject eye by the Rayleigh component of the scattered radiation.

It is a further object of the present invention to provide apparatus and methods essentially eliminating the age-dependent measurement variations previously shown to be present in existing diagnostic techniques.

It is yet another object of the present invention to provide apparatus and methods for monitoring the lens tissue over time for, e.g., evaluating the efficacy of diabetes mellitus treatment or preventative techniques dealing with the prediabetic condition.

Other objects, features, and advantages of the present invention will become apparent with reference to the remainder of the written portion and the drawings of this application.

DETAILED DESCRIPTION

Figure 1:
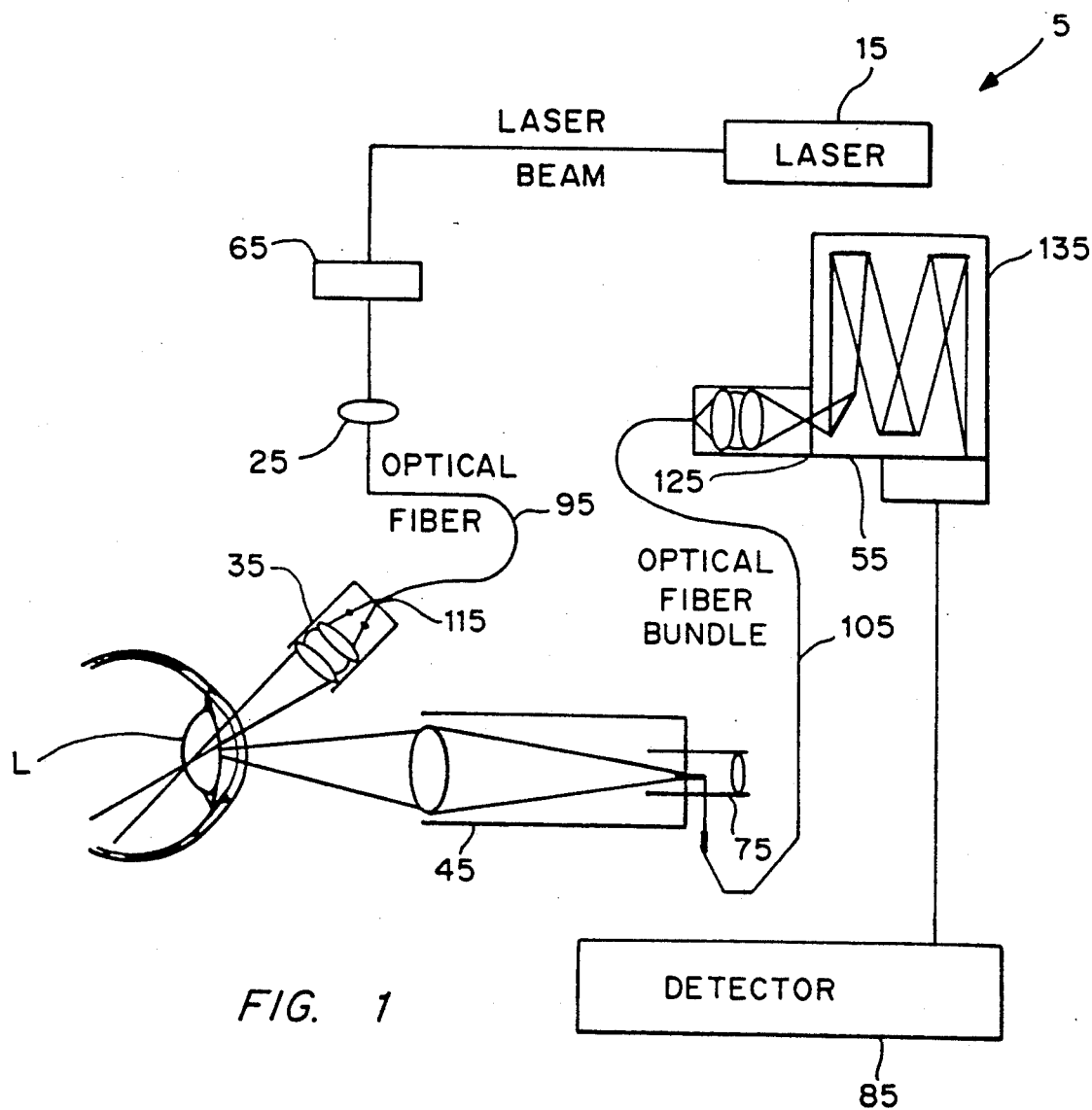
FIG. 1 is a schematic representation of an apparatus of the present invention.

FIG. 1 illustrates an optical system 5 of the present invention. Optical system 5 includes a light source 15, lens 25, a confocal lens system 35, collector 45, and a spectrometer 55. Source 15, which provides narrow-band illumination, typically may be a low power krypton laser tuned to produce radiation having a wavelength between approximately 400–430 nm. In one embodiment of optical system 5, source 15 provides radiation at a wavelength of 406.7 nm. Also shown in FIG. 1 are ocular lens tissue L, attenuator 65, eyepiece 75, detection and processing assembly 85, an fiber optic waveguides 95 and 105.

According to FIG. 1, attenuator 65, used to reduce the power level of the transmitted radiation, receives radiation from source 15 and forwards it to lens 25. Lens 25, which may be a 40× microscope objective or other similar device, then focuses the (attenuated) radiation onto the end of waveguide 95, which in turn transmits the radiation to confocal lens system 35. Lens system 35 subsequently delivers the radiation to a selected volume of ocular lens tissue L (typically approximately 200 cubic micrometers). A modified slit lamp base may be used to house and position lens system 35 for easy access to lens tissue L, while lens system 35 itself is designed to permit the same volume of lens tissue L to be held in the focal point of collector 45. In an embodiment of the present invention consistent with FIG. 1, the aperture 115 of lens system 35 at its focus is greater than approximately fifteen micrometers, ensuring that the excitation radiation diverges rapidly after passing through the focal point of lens system 35 and thereby reducing the spot intensity of the radiation should it encounter any other portions of the ocular tissue.

Collector 4 receives the radiation backscattered from lens tissue L as a result of it being illuminated by radiation from source 15. From collector 45, the backscattered radiation is directed into waveguide 105 and transmitted to the entrance slit 125 of the monochromator 135 forming spectrometer 55. If desired, collector 45 also may direct a portion of the backscattered radiation to eyepiece 75, permitting an operator to view the exact location of the selected volume of lens tissue L.

Division and processing of the backscattered radiation occurs in spectrometer 55 and detection and processing assembly 85. Radiation transmitted to spectrometer 55 initially is separated into its Rayleigh and florescence components. The two components subsequently are directed, respectively and as necessary, to amplifiers forming part of assembly 85, for determination of the intensities of each. Assembly 85 also may include a digital computer or similar computing device for forming the ratio of the fluorescent and Rayleigh components of the backscattered radiation, thereby normalizing the peak intensity of the fluorescent component.

Figure 2:
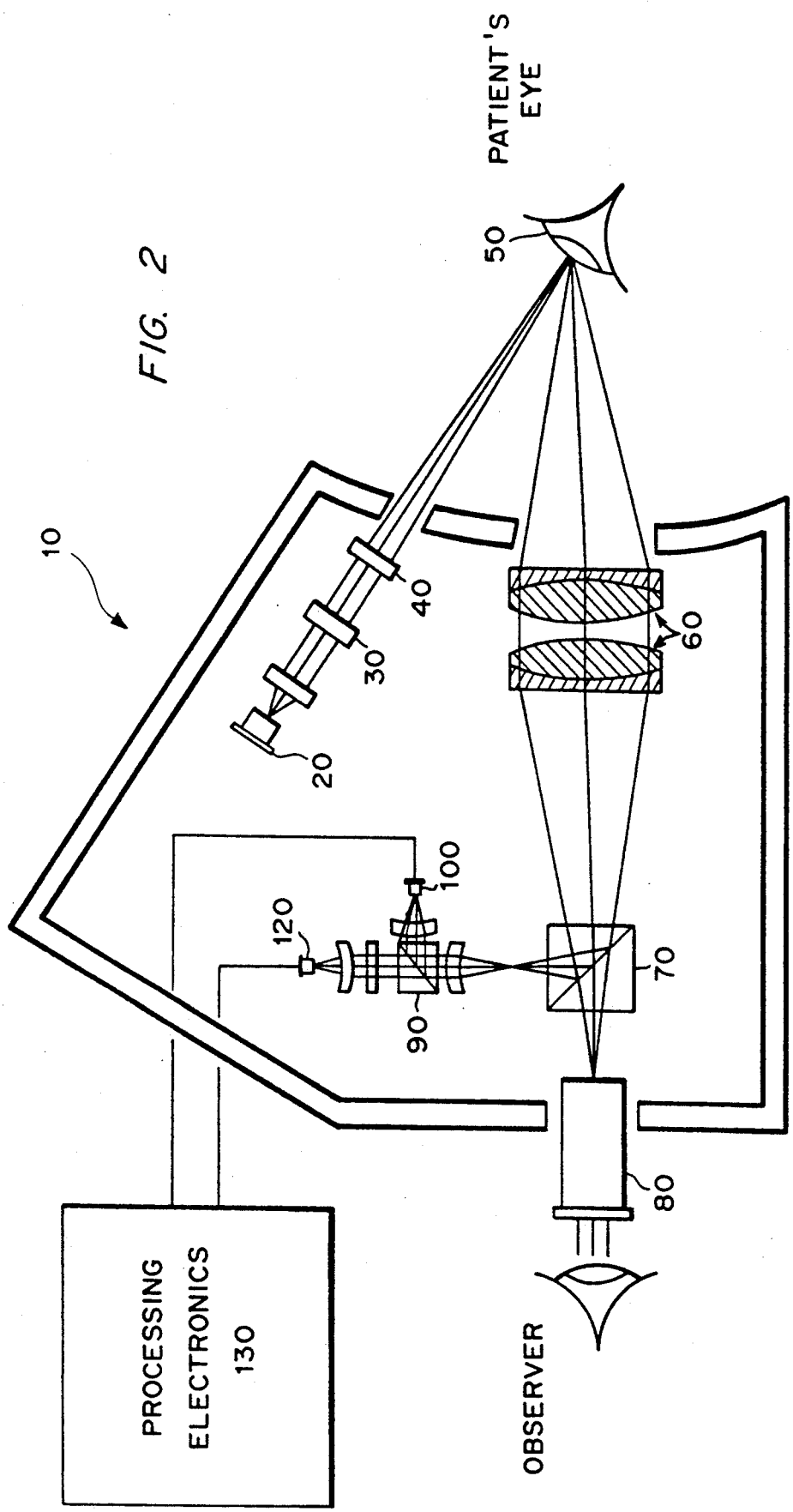
FIG. 2 is a schematic representation of an alternate embodiment of the apparatus of FIG. 1.

An alternate embodiment 10 of optical system 5 is illustrated in FIG. 2. According to FIG. 2, light source 20, which may be a laser diode, produces radiation of wavelength approximately 813.4 nm (within the range of approximately 800–860 nm) and is coupled to a nonlinear frequency doubling device 30 to produce the desired wavelength output of 406.7 nm (within the range 400–430 nm). Light source 20 alternatively may be a laser, light emitting diode, or other narrow-band light source (including broadband sources coupled to optical filters). The radiation subsequently is directed through an optical delivery system 40 into the eye 50 of a patient. As with the optical system 5 of FIG. 1, alternate embodiment 10 includes an optical collector 60 confocal to the delivery system 40 to collect the backscattered radiation from the lens of eye 50. Similarly as noted above, the backscattered radiation collected includes both a fluorescence signal (typically approximately 490-500 nm within the range 460-500 nm, or within the range 520-600 nm) and an intense Rayleigh component at the illumination wavelength.

FIG. 2 additionally discloses means for separating the components of interest of the backscattered radiation, including dichroic beam splitters 70 and 90, and for detecting the intensity of the components simultaneously using single chip silicon detectors 100 and 120 or similar devices. Alternatively, component separation may be accomplished using beam splitters in conjunction with optical bandpass filters or dispersive elements such as diffraction gratings. Hybrid detector/filter assemblies also may be used. Electronic circuitry 130, such as but neither limited to nor necessarily requiring analog amplifiers, analog to digital (A/D) converters, and a digital computer, processes the data detected by detectors 100 and 120, calculates the normalized fluorescent/Rayleigh component ratio, and, if desired, makes the result available to an operator through a digital display or other suitable means. Eyepiece 80, finally, may be used by the operator to view the location of the excitation focal point in eye 50.

The present invention may further be understood with reference to the following non-limiting EXAMPLE.

EXAMPLE

Figure 3:
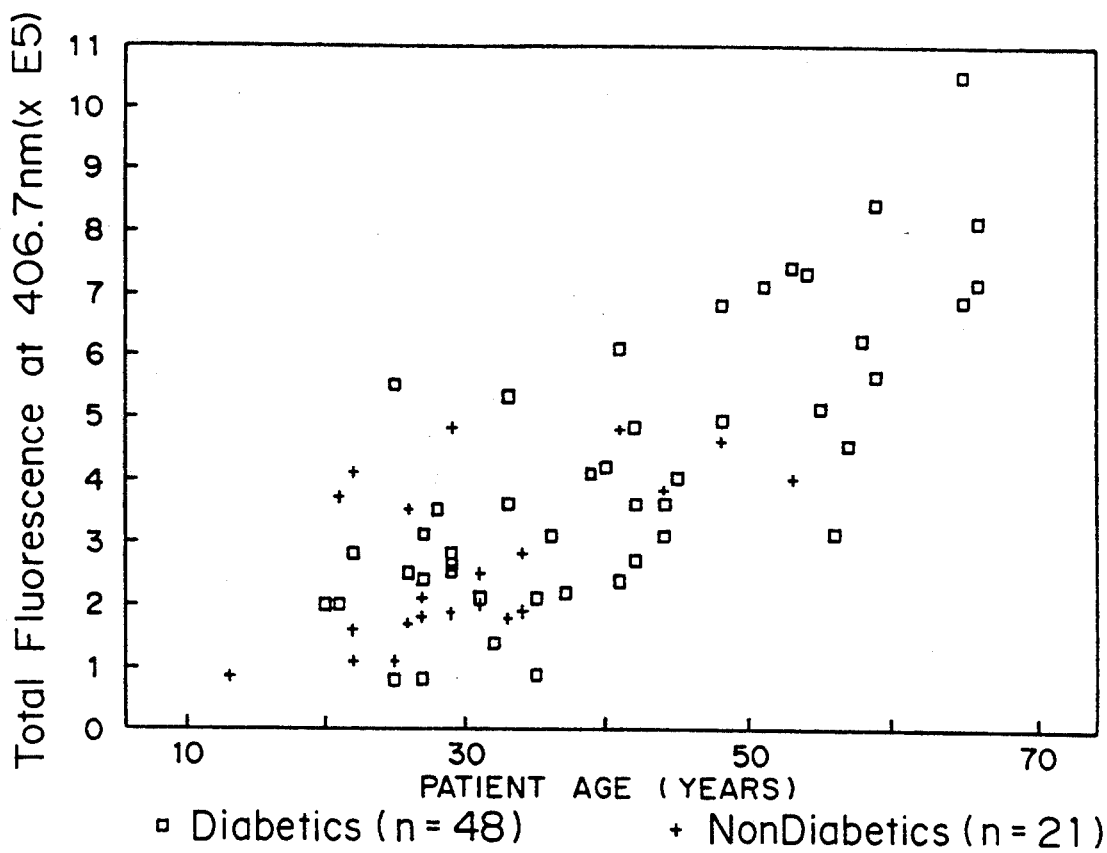
FIG. 3 is a graphical representation of the fluorescent signal intensity as a function of age of both diabetic and nondiabetic patients obtained using the apparatus of FIG. 1 as described in the EXAMPLE herein.
Figure 4:
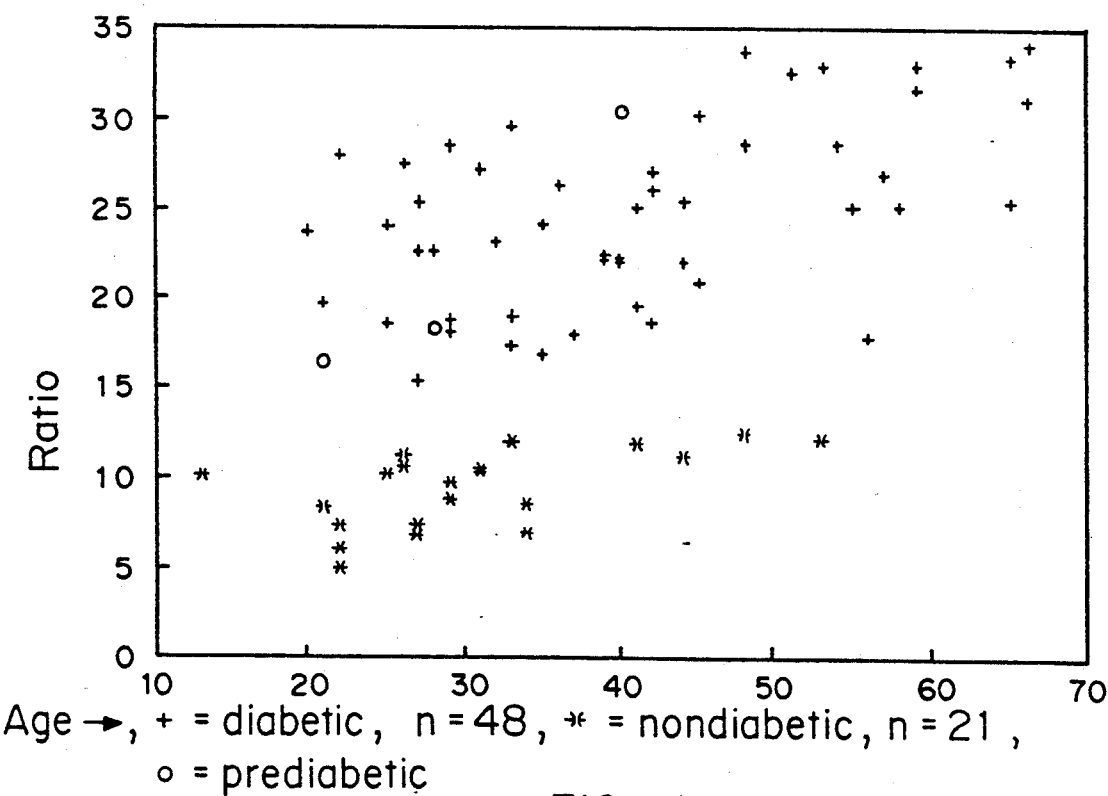
FIG. 4 is a graphical representation of the ratio of the fluorescent to Rayleigh signal intensities as a function of age of both diabetic and nondiabetic patients obtained using the apparatus of FIG. 1 as described in the EXAMPLE herein.

FIGS. 3-6 illustrate data obtained from clinical trials conducted using sixty-nine (69) human patients aged twelve (12) to sixty-five (65). Forty-eight (48) of the patients had previously been diagnosed as having diabetes, while the remaining twenty-one (21) had not. FIGS. 3 shows the total fluorescence signal obtained for each patient (expressed in "Counts $\times 10^5$," where the number of Counts is a function of the number of emitted photons per unit time) using an illumination wavelength of 406.7 nm. FIG. 4 details the results when those same fluorescence signals ar normalized by the Rayleigh component of the backscattered radiation in accordance with the present invention. As illustrated in FIG. 4, although the normalized signals trend upward as a function of age, they evidence clear distinctions between those patients known to have diabetes or the prediabetic condition and those who did not. The normalized signals for the nondiabetics, for example, were less than thirteen (13), while those for diabetics exceeded fifteen (15).

Figure 5:
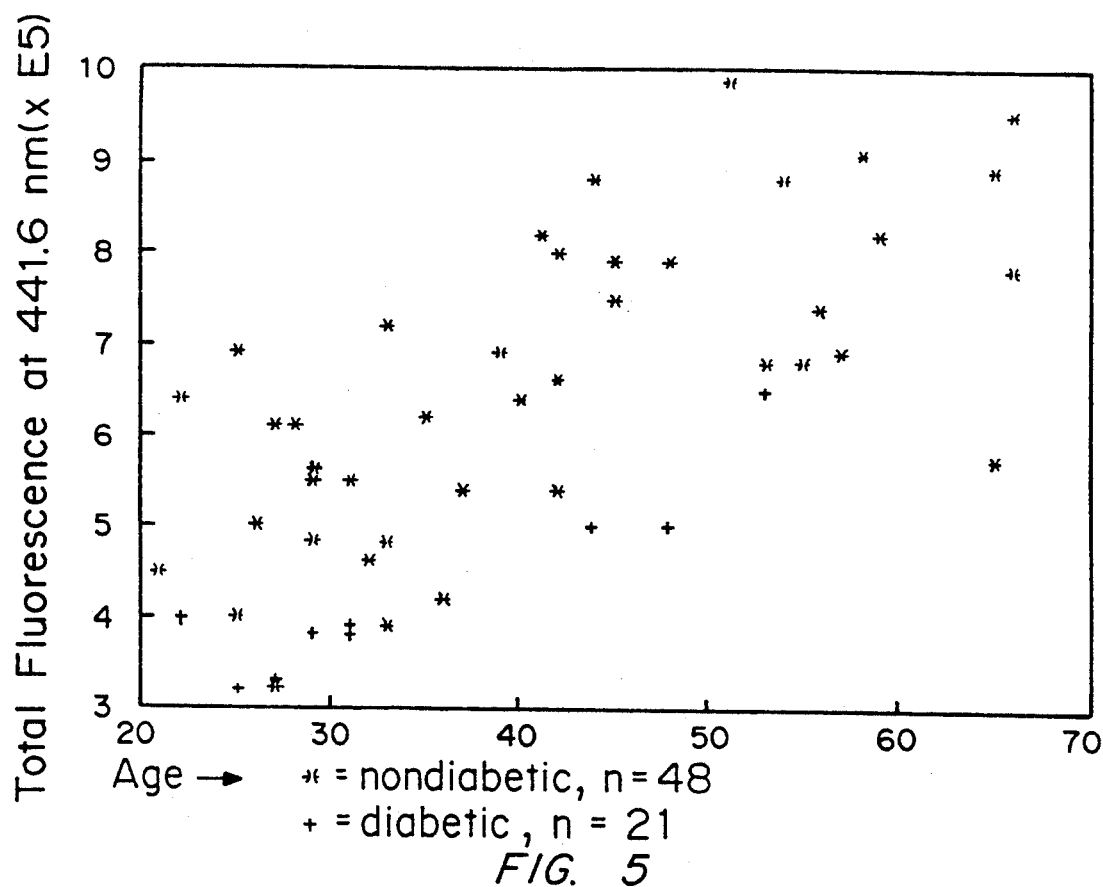
FIG. 5 is a graphical representation of the fluorescent signal intensity as a function of age of both diabetic and nondiabetic patients obtained using the apparatus of FIG. I for an illumination radiation wavelength outside the range of that used in connection with the present invention.
Figure 6:
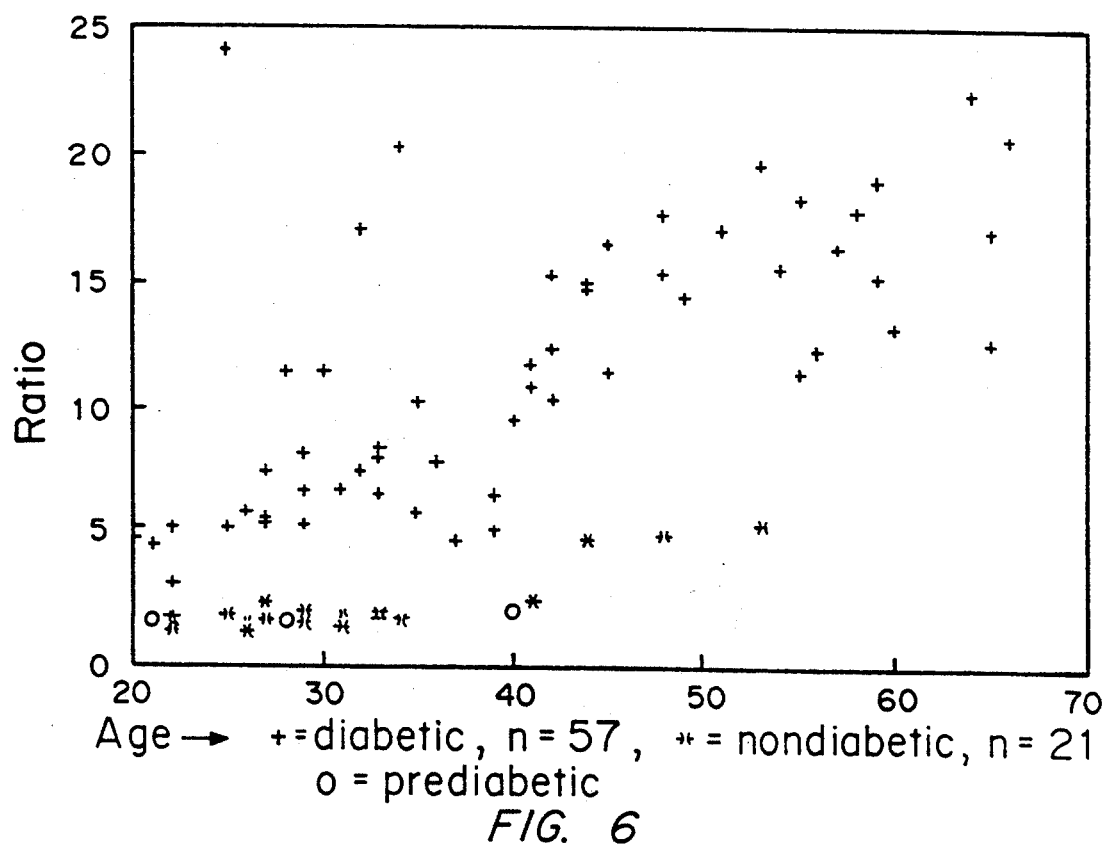
FIG. 6 is a graphical representation of the ratio of the fluorescent to Rayleigh signal intensities as a function of age of both diabetic and nondiabetic patients obtained using the apparatus of FIG. 1 for an illumination radiation wavelength outside the range of that used in connection with the present invention.

By contrast, use of an illumination wavelength of 441.6 nm (outside the range of the present invention) produced much less desirable results. FIGS. 5-6, which correspond, respectively, to FIGS. 3-4, show (in FIG. 6) much less of a distinction between the normalized signals for the diabetic as opposed to nondiabetic patients. Furthermore, those patients who tested ICA positive are shown to have fluorescent/Rayleigh ratios within the range of nondiabetic patient values. As a result, no clearly established threshold is available for diagnostic purposes.

The foregoing is provided for purposes of illustration, explanation, and description of embodiments of the present invention. Modifications and adaptations to these embodiments will be apparent to those of ordinary skill in the art and may be made without departing from the scope or spirit of the invention.

We claim:

1. An apparatus for measuring molecular changes in a patient having an ocular lens that, when illuminated, is capable of backscattering radiation including fluorescent and Rayleigh components of determinable intensities, comprising:
   a. means for illuminating the ocular lens with light having a wavelength between approximately 400-430 nm, thereby causing the ocular lens to backscatter radiation in response to the illumination;
   b. means, responsive to the backscattered radiation, for collecting the backscattered radiation;
   c. means, connected to the collecting means, for separating the backscattered radiation into its fluorescent and Rayleigh components; and
   d. means, connected to the separating means, for (i) detecting the intensity of each of the separated fluorescent and Rayleigh components and (ii) forming the ratio of the detected intensities, thereby producing a measurement of molecular changes in the ocular lens.

2. An apparatus according to claim 1 in which the illuminating means comprises:
   a. a light source selected from the group consisting of lasers, laser diodes coupled to nonlinear frequency doubling devices, light emitting diodes, and broadband sources coupled to optical filters;
   b. a lens, optically responsive to the light from the light source, for focusing the light; and
   c. a lens system, optically responsive to the focused light, having a focus, and defining an aperture at its focus greater than approximately fifteen micrometers.

3. An apparatus according to claim 2 further comprising an eyepiece means, responsive to the backscattered radiation, for permitting an operator to view the ocular lens.

4. An apparatus according to claim 3 in which the separating means comprises at least one dichroic beam splitter.

5. An apparatus according to claim 4 in which the detecting and forming means comprises at least one single chip silicon detector and the wavelength of the fluorescent component of the backscattered radiation is selected from the group consisting of between approximately 460-500 nm and 520-600 nm.

6. An apparatus according to claim 5 in which the detecting and forming means further comprises an amplifier.

7. An apparatus according to claim 6 in which the illuminating means further comprises means for adjusting the power level of the illuminating light.

8. An apparatus for measuring molecular changes in a patient having an ocular lens having a volume that, when illuminated, is capable of backscattering radiation including fluorescent and Rayleigh components of determinable intensities, comprising:
   a. a laser for providing light having a selected wavelength and power level;
   b. means, optically responsive to the provided light, for adjusting the power level of the light;
   c. a lens, optically connected to the adjusting means, for focussing the light;
   d. a first optical fiber, optically connected to the lens, for receiving the focused light;

e. a lens system, optically connected to the first optical fiber and defining an aperture having a focus greater than approximately fifteen micrometers, for delivering the focused light to a selected approximately two hundred micrometers of the volume of the ocular lens, thereby causing the ocular lens to backscatter radiation in response to the delivered light;

f. a collector (i) having a focal point encompassing the selected volume of the ocular lens to which the focused light is delivered and (ii) responsive to the backscattered radiation, for collecting the backscattered radiation;

g. a second optical fiber, optically connected to the collector, for receiving the collected radiation;

h. means, connected to the connecting means, for separating the backscattered radiation into its fluorescent and Rayleigh components; and i. means, connected to the separating means, for (i) detecting the intensity of each of the separated fluorescent and Rayleigh components and (ii) forming the ratio of the detected intensities, thereby producing a measurement of molecular changes in the optical lens.

9. An apparatus according to claim 8 in which the wavelength is approximately 406.7 nm, the separating means is a spectrometer, and the detecting and forming means comprises a computer.

10. An apparatus according to claim 9 further comprising an eyepiece means responsive to the backscattered radiation, for permitting an operator to view the selected volume of the ocular lens, and in which the measured molecular changes assist in diagnosing conditions selected from the group consisting of diabetes, the prediabetic condition, and cataracts.

11. An apparatus according to claim 8 in which the separating means comprises at least one dichroic beam splitter.

12. An apparatus according to claim 11 further comprising an eyepiece means responsive to the backscattered radiation, for permitting an operator to view the selected volume of the ocular lens, and in which the measured molecular changes assist in diagnosing conditions selected from the group consisting of diabetes, the prediabetic condition, and cataracts.

13. A method for measuring molecular changes in a patient having tissue that, when illuminated, is capable of backscattering radiation including fluorescent and Rayleigh components of determinable intensities, comprising the steps of:

a. illuminating the tissue with light having a wavelength selected from the group consisting of between approximately 400–430 nm and between approximately 800–860, thereby causing the tissue to backscatter radiation in response to the illumination;

b. separating the backscattered radiation into its fluorescent and Rayleigh components;

c. detecting the intensity of each of the separated fluorescent and Rayleigh components; and d. forming the ratio of the detected intensities.

14. A method according to claim 13 in which the illuminating step comprises the steps of:

a. providing a light source selected from the group consisting of lasers, laser diodes coupled to nonlinear frequency doubling devices, light emitting diodes, and broadband sources coupled to optical filters, for emitting the light at a wavelength of approximately 406.7 nm; and b. focusing the light using a lens system having a focus and defining an aperture at its focus greater than approximately fifteen micrometers; and further comprising the step of comparing the ratio of the detected intensities against at east one preselected value for assisting in diagnosing conditions selected from the group consisting of diabetes and the prediabetic condition.

15. A method according to claim 14 in which the detecting step comprises the step of detecting the separated fluorescent component at a wavelength selected from the group consisting of between approximately 460–500 nm and 520–600 nm and in which the comparing step comprises the step of comparing the ratio of the detected intensities against two preselected values, thirteen and fifteen, so that if the ratio is less than thirteen the patient may be diagnosed as unlikely to have the selected condition and if the ratio is greater than fifteen the patient may be diagnosed as likely to have the selected condition.

16. A method according to claim 15 in which the separating step comprises the step of separating the backscattered radiation using at least one dichroic beam splitter.

* * * * *

UNITED STATES PATENT AND TRADEMARK OFFICE
CERTIFICATE OF CORRECTION

PATENT NO. : 5,203,328

DATED : April 20, 1993

INVENTOR(S) : Mark A. Samuels, et al.

It is certified that error appears in the above-identified patent and that said Letters Patent is hereby corrected as shown below:

```
Column 3, line 12, delete the word "threshol-" and
insert --threshold--

Column 3, line 13, delete the letter "d" at the
beginning of the line

Column 3, line 59, delete "FIG. I" and insert
--FIG. 1--

Column 4, line 36, delete "4" and insert --45--
```

Signed and Sealed this

Fourth Day of January, 1994

*Attest:*

BRUCE LEHMAN

*Attesting Officer*     Commissioner of Patents and Trademarks